United States Patent [19]

Current

[11] Patent Number: 4,625,051
[45] Date of Patent: Nov. 25, 1986

[54] CARBOXYLIC ACID ESTER HOMOLOGATION USING A SULFIDED COBALT CATALYST

[75] Inventor: Steven P. Current, Novato, Calif.

[73] Assignee: Chevron Research Company, San Francisco, Calif.

[21] Appl. No.: 507,306

[22] Filed: Jun. 23, 1983

[51] Int. Cl.$^4$ .............................................. C07C 67/36
[52] U.S. Cl. ............................ 560/265; 260/410.9 R; 560/114; 560/204; 560/232; 562/517; 568/876; 568/885
[58] Field of Search ............... 560/232, 265, 114, 204; 260/410.9 R; 568/876, 885, 902, 907

[56] References Cited

U.S. PATENT DOCUMENTS 2,593,440 4/1952 Hagemeyer et al. ............... 560/232
4,189,441 2/1980 Braca et al. ......................... 568/907
4,304,946 12/1981 Isogai et al. ........................ 568/902
4,431,835 7/1981 Gauthier-Lafaye et al. ....... 560/105
4,482,497 11/1984 Rizkalla .............................. 260/413

FOREIGN PATENT DOCUMENTS 34374 8/1981 European Pat. Off. ........... 568/907

Primary Examiner—Vivian Garner
Attorney, Agent, or Firm—T. G. DeJonghe; C. J. Caroli

[57] ABSTRACT

A process for the conversion of carboxylic acid esters to homologous carboxylic acid esters which comprises reacting a carboxylic acid ester having from two to about twenty carbon atoms with hydrogen and carbon monoxide in the presence of a heterogeneous sulfided catalyst comprising cobalt, optionally in admixture with a co-catalyst selected from the elements of Group VI-B of the Periodic Table.

6 Claims, No Drawings

CARBOXYLIC ACID ESTER HOMOLOGATION USING A SULFIDED COBALT CATALYST

BACKGROUND OF THE INVENTION

The present invention is concerned with a process for the homologation of carboxylic acid esters. More specifically, the present invention involves a process for the conversion of carboxylic acid esters to homologous carboxylic acid esters by reaction of the ester with hydrogen and carbon monoxide in the presence of a heterogeneous sulfided catalyst.

An article by M. Hidai et al. in Bull. Chem. Soc. Japan, volume 55, pages 3951-52 (1982) describes the homologation of methyl esters, in particular the conversion of methyl acetate to ethyl acetate, with synthesis gas in the presence of a homogeneous ruthenium-cobalt catalyst and a methyl iodide promoter.

European Patent Application Publication No. 0031606 A1 describes the preparation of carboxylic acids and esters from carboxylic acid esters having one less carbon atom, carbon monoxide and hydrogen in the presence of a catalyst containing a ruthenium compound, a Group II metal iodide and/or bromide and a further Group VIII metal compound.

European Patent Application Publication No. 0031784 A2 describes the preparation of alkyl carboxylates from lower homologs by reaction with carbon monoxide and hydrogen using a ruthenium, cobalt and iodide catalyst system.

European Patent Application Publication No. 0046128 A1 describes the hydrocarbonylation and/or carbonylation of alkyl carboxylates in the presence of ruthenium, cobalt, vanadium and an iodide promoter.

SUMMARY OF THE INVENTION

The present invention relates to a process for the conversion of carboxylic acid esters to homologous carboxylic acid esters which comprises reacting a carboxylic acid ester having from two to about twenty carbon atoms with hydrogen and carbon monoxide at a temperature in the range of about 150° C. to 350° C. and a pressure in the range of about 500 psig to 5,000 psig in the presence of a heterogeneous sulfided catalyst comprising cobalt, optionally in admixture with a co-catalyst selected from the elements of Group VI-B of the Periodic Table.

Among other factors, the present invention is based on my discovery that carboxylic acid esters can be converted to useful oxygenated products having at least one more carbon atom than the starting ester in improved yield and selectivity by utilizing a heterogeneous sulfided catalyst system.

An advantage of the present process lies in the fact that the heterogeneous catalyst employed is easier to separate from the reaction products than the homogeneous catalysts of the prior art.

In addition, it has been found that the present process does not require any souble promoters or co-catalysts. This is particularly advantageous, since the absence of a halide promoter in the system obviates the need for expensive corrosion resistant equipment.

Oxygen-containing carbon compounds obtained with high selectivity in the process of the invention are carboxylic acid esters or the secondary products which may be formed therefrom under the reaction conditions in a subsequent reaction, for example, transesterification, reduction, hydrolysis, condensation or dehydration.

DETAILED DESCRIPTION OF THE INVENTION

Illustrative of a typical batch procedure, the ester is charged to a high pressure reactor, and then there is introduced a heterogeneous sulfided catalyst system comprising cobalt and, optionally, an element of Group VI-B of the Periodic Table. The reactor is pressurized with a mixture containing carbon monoxide and hydrogen and heated for a suitable length of time to give the desired conversion. Liquid and gaseous products and reactants can be easily separated from the catalyst by filtration, distillation or other methods. Unreacted starting materials can be recycled. The products can be isolated by a number of known methods, including distillation. In some cases it may be advantageous to further process the products. For example, ethyl propionate can be easily hydrolyzed to propionic acid.

The process of the present invention can also be run in a continuous fashion. This is particularly advantageous as the catalyst is not soluble in the reaction medium. A number of reactor configurations are suitable including fixed and fluid beds, slurry beds and stirred tank reactors. As with a batch reaction, unreacted starting materials can be easily recycled and, if desired, the products can be further processed.

The carboxylic acid esters suitable for use in the present invention will generally contain from two to about twenty, preferably two to six, carbon atoms. Preferred carboxylic acid esters include methyl acetate and ethyl acetate. If desired, the reactant ester may be diluted with an ester-miscible solvent such as dioxane, tetrahydrofuran, N-methylpyrrolidinone, and the like. When methyl acetate is used as the starting ester, the reaction product predominantly formed is ethyl acetate, with lesser amounts of acetic acid, methanol and ethanol.

The heterogeneous sulfided catalyst system employed in the present process comprises a composite of sulfides of a cobalt component and, optionally, a Group VI-B component. Group VI-B co-catalysts suitable for admixture with the cobalt component include chromium, molybdenum and tungsten. A particularly preferred catalyst system comprises cobalt and molybdenum. In addition, the catalyst system may optionally contain phosphorus or silicon.

In carrying out the reaction, it is usually desirable, although not essential, to place the catalyst on a support. Various supports suitable for use in the process are described in the prior art. Generally, the support should be a solid, inert material which is relatively insoluble in the solvent employed. Suitable supports include various treated or untreated organic and inorganic supports. Included among these are synthetic and naturally occurring polymers, alumina, silica, titania, silica-alumina, zeolites, glass, carbon, and the like. Particularly preferred supports are alumina and silica-alumina.

The metals may be added to the support using a number of methods known to the art such as by impregnation, co-precipitation, and the like. The method of loading the catalyst on the support will depend on the nature and composition of the support. Generally, the most convenient method of depositing the metals on the support is by adding a solution of metal salts to the support and subsequently converting them to an insoluble form.

An especially suitable catalyst precursor may be prepared by impregnating alumina with an aqueous or organic solution of the metal salts, either together or sequentially, followed by drying and calcining to give the metal oxides.

The catalyst may be converted to its active sulfide form by any of a number of conventional procedures. Treatment with hydrogen sulfide or other sulfur-containing compounds such as carbon disulfide, dimethyl disulfide or sulfur, in the presence of hydrogen or synthesis gas is effective. This treatment can be either prior to or concurrent with the ester carbonylation reaction.

In the process of the present invention carboxylic acid esters are reacted with carbon monoxide and hydrogen (synthesis gas). Synthesis gas produced by the reaction of carbonaceous material with water is suitable. Mixtures of carbon dioxide and hydrogen, carbon monoxide and water, and the like, may also be employed. Whether introduced originally, or produced in situ under processing conditions, the reaction elements of carbon monoxide and hydrogen are required.

The relative molar quantities of carbon monoxide and hydrogen present during the reaction can vary in the range between about 10:1 and 1:10, and preferably in the range between about 3:1 and 1:3. An inert diluent gas such as nitrogen or helium may be included if desired.

The carbonylation reaction requires a relatively high pressure for optimum selectivity and yield of product. The pressure is maintained in the range between about 500 psig and 5,000 psig, and preferably in the range between about 800 psig and 2000 psig.

The reaction is conducted at a temperature in the range between about 150° C. and 350° C., and preferably in the range between about 190° C. and 290° C.

The time that the reactants are in contact with the catalyst will be dependent, among other factors, on the temperature, pressure, ester reactant, catalyst, reactor configuration and the desired level of conversion.

The solid catalyst can be easily separated from the generally liquid and gaseous reaction products and unreacted starting materials by, for example, filtration, centrifugation, settling out or distillation. The catalyst can be reused in a subsequent reaction. Unreacted starting materials can be separated from reaction products and are suitable for recycle in the process.

The products of the reaction, which can be isolated by a number of well-known methods such as distillation, are generally useful as solvents or chemical intermediates. In some cases it may be advantageous to further process the reaction products by well-known means to other useful products. For example, ethyl propionate can be hydrolyzed to propionic acid.

The following examples are provided to illustrate the invention in accordance with the principles of this invention but are not to be construed as limiting the invention in any way except as indicated by the appended claims.

Examples

EXAMPLE 1

An 18 ml stainless steel reactor was charged with 5.0 ml of methyl acetate and 0.5 g of a catalyst comprising cobalt (3%) and molybdenum (12%) oxides, supported on alumina, that had been pretreated with 10% hydrogen sulfide in hydrogen at 325° C. Also included was 0.10 ml of 1,4-dioxane to serve as a gas chromatography reference. The reactor was pressurized to 900 psi with a 2:1 mixture of hydrogen and carbon monoxide and heated with shaking to 240° C. for four hours. Analysis of the liquid product indicated the formation of ethyl acetate (2.3 mmol) and acetic acid (3.1 mmol) as major products. Lesser amounts of ethanol and methyl formate were also formed.

EXAMPLES 2-6

A stainless steel reactor tube was charged with 7.23 g of a catalyst comprising cobalt (3.2%), molybdenum (12.4%) and phosphorus (1.7%) oxides supported on alumina. The catalyst was treated with 10% hydrogen sulfide in hydrogen at 325° C. until water formation ceased, then purged with nitrogen. Synthesis gas, comprising two parts hydrogen and one part carbon monoxide, and methyl acetate were passed over the catalyst at the rate, pressure, temperature and time indicated in Table 1. The methyl acetate contained a small amount of toluene to serve as a standard for gas chromatography analysis. The GHSV reported is for the exit gases. The average rates of product formation, as determined by on-line gas chromatography, are also reported in Table 1.

TABLE 1

|  | Example 2 | Example 3 | Example 4 | Example 5 | Example 6 |
| --- | --- | --- | --- | --- | --- |
| REACTION CONDITIONS |  |  |  |  |  |
| Temperature, °C. | 240 | 250 | 250 | 250 | 250 |
| Pressure, psi | 1575 | 1580 | 2060 | 2000 | 2035 |
| GHSV (off gas) | 2375 | 2302 | 2555 | 1935 | 1238 |
| LHSV (feed) | .71 | .65 | .71 | .36 | .41 |
| Time at Condition, hr | 17.92 | 23.83 | 21.25 | 23.92 | 26.22 |
| PRODUCTS, MMOL/HR |  |  |  |  |  |
| Methane | 1.15 | 2.08 | 2.63 | 4.04 | 5.00 |
| Carbon Dioxide | .78 | 1.74 | 1.76 | 2.27 | 2.19 |
| Water | 10.65 | 14.91 | 15.27 | 12.56 | 12.59 |
| Dimethyl Ether | 2.06 | 3.09 | 3.72 | 2.91 | 2.39 |
| Methanol | 5.52 | 7.50 | 8.28 | 5.15 | 5.23 |
| Methyl Ethyl Ether | .33 | .80 | 1.08 | 1.51 | 1.20 |
| Ethanol | 2.07 | 3.74 | 4.48 | 5.99 | 6.11 |
| Methyl Acetate (feed) | 41.06 | 33.84 | 31.19 | 9.12 | 9.46 |
| Ethyl Acetate | 8.41 | 10.16 | 10.41 | 5.54 | 5.68 |
| Acetic Acid | 1.55 | 2.00 | 1.56 | 1.57 | 2.29 |
| Toluene, internal std. | 2.19 | 2.19 | 2.19 | 1.10 | 1.10 |

What is claimed is:

1. A process for the conversion of carboxylic acid esters to homologous carboxylic acid esters which comprises reacting a carboxylic acid ester having from two to about twenty carbon atoms with hydrogen and carbon monoxide at a temperature in the range of about 150° C. to 350° C. and a pressure in the range of about 500 psig to 5,000 psig in the presence of a heterogeneous sulfided-catalyst comprising a composite of sulfides of a cobalt component and a Group VI-B element component cocatalyst and in the absence of a halide promoter.

2. The process according to claim 1, wherein the co-catalyst is molybdenum.

3. The process according to claim 1, wherein the sulfided catalyst further comprises phosphorus or silicon.

4. The process according to claim 1, wherein the sulfided catalyst is present on a support.

5. The process according to claim 4, wherein the support is alumina or silica-alumina.

6. The process according to claim 1, wherein methyl acetate is converted to ethyl acetate.

* * * * *